United States Patent [19]

Kung et al.

[11] Patent Number: 4,963,658
[45] Date of Patent: Oct. 16, 1990

[54] DNA DETECTION METHOD

[75] Inventors: Viola T. Kung, Menlo Park; Peter A. Nagainis, San Jose; Edward L. Sheldon, III, Menlo Park, all of Calif.

[73] Assignee: Molecular Devices Corporation, Palo Alto, Calif.

[21] Appl. No.: 285,895

[22] Filed: Dec. 15, 1988

Related U.S. Application Data

[63] Continuation-in-part of Ser. No. 93,361, Sep. 4, 1987.

[51] Int. Cl.$^5$ .................. C07 15/00; G01N 33/566; C12Q 1/68; C12N 11/02
[52] U.S. Cl. .................. 530/406; 536/402; 536/387; 536/350; 435/6; 435/7; 435/177; 436/501
[58] Field of Search ............... 530/402, 406, 387, 350; 435/6, 7, 177; 436/501

[56] References Cited

U.S. PATENT DOCUMENTS 4,493,899  1/1985  Smith et al.

FOREIGN PATENT DOCUMENTS 0135159   8/1984   European Pat. Off.
0147665 A1 11/1984 European Pat. Off.
0131830   1/1985   European Pat. Off.
WO85/05685 12/1985 PCT Int'l Appl.
2125964 A  7/1983  United Kingdom.

OTHER PUBLICATIONS

Syvanen et al., Nuclear Acid Research, vol. 13, pp. 2789–1802, 1985.
Voller et al. in Manual of Clinical Laboratory Immunology, 3rd edition, Eds: Rose, Friedman & Fahey, 1986.
Tijssen, Practice & Theory of Enzyme Immunoassays, vol. 15, Elsevier Press, 1985, see Chapter 11, pp. 221–230, 259–261.
Vogelstein et al., *PNAS, U.S.A.*, 76:615–619, (1979).
Gellert, *The Enzymes*, 14:345–367, (1981).
Wang, *The Enzymes*, 14:332–343.
Chase et al., *Ann. Rev. Biochem.*, 55:103–136, (1986).
Kowalczykowski et al., *Biochemistry*, 17:425–429, (1978).
Krauss et al., *Biochemistry*, 20:5346–5352, (1981).
Kung et al., *The Journal of Biological Chemistry*, 252:5398–5402, (1977).
DuClos et al., *Journal of Immunological Methods*, 88:185–192, (1986).
"Investigation of Complexes Formed Between Gene 32 Protein from Bacteriophase T-4 and Heavy-Atom-Modified Single-Stranded Polynucleotides Using Optical Detection of Magnetic Resonance," by Khamis et al., *Biochemistry* (1986), 25:5865–5872.
"Deoxyribonucleic Acid Topoisomerase I from Chicken Erythrocytes: Purification, Characterization, and Detection by a DNA Binding Assay," by Tricoli et al., *Biochemistry* (1983) 22:(8)2025–2031.
"Large-Scale Overproduction and Rapid Purification of the *Escherichia coli* SSB SSB Gene Product. Expression of the SSB Gene under $\lambda$ $P_L$ Control," by Lohman et al., *Biochemistry* (1986) 25:21–25.

*Primary Examiner*—Christine Nucker
*Assistant Examiner*—Karen I. Krupen
*Attorney, Agent, or Firm*—Allegretti & Witcoff, Ltd.

[57] ABSTRACT

Picogram amounts of DNA can be detected in a sample by the use of high-affinity, single-stranded DNA binding proteins. The assay is applicable not only to pure DNA samples but also to samples containing significant amounts of protein.

6 Claims, No Drawings

DNA DETECTION METHOD

CROSS-REFERENCE TO RELATED APPLICATION

This application is a continuation in part of U.S. application Ser. No. 093,361 filed Sept. 4, 1987, which disclosure is hereby incorporated by reference.

INTRODUCTION

1. Technical Field

This invention relates to methods for detecting the presence of DNA. The method employs high affinity binding proteins for single stranded DNA.

2. Background

The amount of DNA in a sample has traditionally been measured either by spectrophotometric means or fluorometrically with the use of ethidium bromide. If the sample is pure (does not contain significant amounts of contaminants such as other nucleic acids, protein, phenol, or agarose) the spectrophotometric measurement of the amount of ultraviolet (UV) irradiation absorbed is simple and accurate. However, if there is contamination with protein or compounds which absorb strongly in the UV, such as phenol, accurate quantitation of the amount of DNA will not be possible. Furthermore, this technique is only suitable for samples containing DNA in the μg/ml range.

If the amount of DNA in the sample is small, or if the sample contains significant quantities of impurities, the amount of DNA may be estimated from the intensity of UV-induced fluorescence emitted by ethidium bromide intercalated into the DNA. The amount of fluorescence is proportional to the total amount of DNA. The quantity of DNA in the sample therefore can be estimated by comparing the fluorescent yield of the sample with that of a series of standards. As little as 1 to 5 μg/ml of DNA can be detected by this method. With the use of a minifluorometer (such as that manufactured by Hoefer Scientific Instruments, San Francisco, Calif.) and the fluorochrome Hoechst 33258, the sensitivity may be increased to 10 ng/ml.

With the advent of recombinant DNA technology, it has become imperative to be able to identify significantly lower concentrations of DNA in a sample, for example, any contaminating DNA which may be present in a recombinant product. The contaminating DNA may be non-specific and of unknown sequence. Therefore, enzyme amplification of sample DNA (using for example the DNA polymerase chain reaction method) is difficult for lack of universal primers for DNA synthesis. There is, therefore, substantial interest in being able to detect rapidly and accurately the presence of extremely small amounts of DNA.

RELEVANT LITERATURE

Krauss et al., *Biochemistry* (1981) 22:5346-5352 disclose the binding of single-stranded binding proteins from *E. coli* to oligonucleotides. Vogelstein and Gillespie, *Proc. Natl. Acad. Sci. U.S.A.* (1979) 76:615-619 disclose the binding of DNA to glass. Kung et al. disclose the purification of topoisomerase I from *Micrococcus luteus* by high salt elution from a DNA-sepharose column; *J. Biol. Chem.* (1977) 252:5398-5402. The following are review articles pertaining to DNA binding proteins. Gellert, *The Enzymes*, Vol. XIV (1981) 345-366; Wang, *The Enzymes*, Vol. XIV (1981) 332-343; Chase, *Ann. Rev. Biochem.* (1986) 55:103-136; Kowalczykowski et al., *The Enzymes*, Vol. XIV (1981) 375-444.

SUMMARY OF THE INVENTION

A novel method is provided for detecting the presence of DNA in a sample, which employs a DNA-detection system in which one of the components is a DNA binding protein which has high affinity for single-stranded DNA (ssDNA). To detect the presence of DNA, a sample, optionally pretreated if it contains protein, is denatured to yield ssDNA. The sample is then contacted with a high-affinity, single-stranded DNA binding protein (BP) to form ssDNA-BP complexes which may then be detected by means of a label bound to either the ssDNA or the BP. The BP and the ssDNA may both be in solution, at the time of contacting, or either of the ssDNA or the BP may be bound non-diffusively to a solid support prior to the time of contacting. When bound to the solid support, the ssDNA or the BP may be bound directly to the solid support or bound by means of a linker molecule. The method may be used to detect DNA in, for example, recombinant protein products, or to detect contaminating organisms in a sample.

DESCRIPTION OF THE SPECIFIC EMBODIMENTS

In accordance with the subject invention, methods and compositions are provided for detecting the presence of DNA in a sample, particularly in a protein product produced in culture, for example, fermentation. The presence of DNA may be detected by the use of high affinity, single-stranded DNA binding proteins.

The method employs single-stranded DNA binding proteins, which may serve to capture and or label single-stranded DNA. The single-stranded DNA binding protein may be bound to a support or free in solution. When free in solution, the single-stranded DNA binding protein will normally be labeled. A sample, usually substantially free of protein, is contacted with a support which binds DNA non-specifically or has, non-diffusively bound to the support, a protein which binds single-stranded DNA specifically.

The single-stranded DNA binding protein (BP) may be from any source, either eukaryotic or prokaryotic, and may include single-stranded DNA binding proteins, topoisomerase, and DNA unwinding proteins. Of particular interest are single-stranded DNA binding protein from *E. coli* (SSB), T4 gene 32 protein and topoisomerase I from *Micrococcus luteus* and *E. coli*. Methods of isolation include affinity chromatography as described in Lohman et al., *Biochemistry* (1986) 25:21-25. BP is also commercially available, for example, from United States Biochemical Corporation, Cleveland, Ohio.

The DNA binding protein is characterized as having high affinity for single-stranded DNA (ssDNA), at least $10^5$ $M^{-1}$, usually in the range of about $10^8$-$10^{10}$ $M^{-1}$ when the ssDNA is at least 100 nucleotides long. Alternatively, the protein may be characterized as a single-stranded DNA binding protein requiring a concentration of greater than about 0.4M sodium chloride (or other monovalent salt providing comparable ionic strength) for elution from ssDNA-cellulose or ssDNA-sepharose. Generally the concentration for elution is greater than about 0.6M sodium chloride, and preferably greater than about 1.0M sodium chloride. When determining the affinity, an aqueous buffer, pH 6 to 9 at 25° C. should be used. No detergent, denaturant (for example, urea, guanidium chloride), chaotropic agent or organic solvent should be present in the buffer.

The BP can be used unbound to any other component, and/or it can be non-diffusively bound, covalently or adsorptively, to a solid support either directly or through a linker molecule or covalently to a label. When a linker molecule is used, the BP is bound to one half of a specific binding pair, the other half being the linker molecule. Examples of specific binding pairs include biotin and anti-biotin; avidin and streptavidin.

For immobilization of BP, solid support materials may be employed. Thus the solid support may include filter membranes, preferably Immobilon TM or nitrocellulose. For nitrocellulose membranes, the pore size of the membrane is less than $5\mu$, preferably less than $1\mu$; and is usually greater than $0.05\mu$, preferably greater than $0.1\mu$. Conventional procedures as appropriate are used for non-diffusive binding of the BP to the solid support. Methods include covalent binding by reaction with carbonyl or imidazole groups, or other active groups present on the membrane, or non-covalently by adsorption to the membrane.

The solid support material may also include chromatographic bed materials, monodisperse latex particles, including those based on styrene, chemically-modified styrene, propylene, methacrylate, butadiene, acrylonitrile or other monomers; polyglutaraldehyde microspheres (e.g., as manufactured by Polysciences, Inc.), nylon beads, chemically-modified nylon beads, oxirane acrylic beads such as Eupergit® (Rohm Pharma, Darmstadt, W. Germany); copolymers of acrylic ester and acrylic amide. Methods of binding BP to these materials include the following: BP may be covalently bound to an activated chromatographic resin having reactive groups capable of forming covalent bonds with proteins, such as CNBr-activated Sepharose-4B, CNBr-activated 4% Agarose or CNBr-activated Sepharose-6MB (Pharmacia P-L Biochemicals; Piscataway, N.J.), or other resin, such as cellulose, by conventional means. BP may be bound to polystyrene beads by non-specific adsorption. BP may also be bound covalently to polystyrene beads containing carboxyl or amino functional groups (Polysciences, Inc.; Warrington, Pa.) by conventional means.

The DNA, generally denatured to single-stranded DNA (ssDNA), can be bound non-diffusively to a solid support, either absorptively or covalently, either directly or through a linker molecule. For absorptive binding, the solid support can be a membrane such as nitrocellulose. The sample containing the ssDNA is preferably filtered onto the membrane. To facilitate binding to the membrane, the salt concentration of the sample is generally greater than 50 mM sodium chloride, preferably greater than 100 mM sodium chloride, or other salt providing similar ionic strength. The ssDNA is then fixed on the membrane by, for example; baking the membrane at between 75° C. and 100° C., preferably at 80° C. for at least 30 minutes, usually for at least 1 hour, and preferably no more than 6 hours; or by washing the membrane with ethanol. When the DNA is bound to the solid support through a linker molecule, the linker molecule may be any molecule which has high affinity for DNA, such as an antibody to DNA, a BP, or the like. In a preferred method, the linker molecule comprises a conjugate of biotin and anti-DNA or biotin and BP bound non-diffusively to the solid support through avidin.

The solid support can also be positively-charged nylon, such as beads or membranes (for example Nytran® (Schleicher and Schull, Inc.; Keene, N.H.), Gene-Screen Plus TM (duPont Company; Boston, Mass.), Zeta-Probe® (BioRad Labs; Pinole, Calif.), Bio-Trace TM (Gelman Sciences, Inc.; Ann Arbor, Mich.), Bio-dyne B® (Pall Biosupport; Glen Cove, N.Y.), and Genatran TM (Plasco, Inc.; Woburn, Mass.)). The ssDNA can be selectively non-diffusively bound to the positively-charged nylon by incubating the nylon in a buffer at between pH 6 and 9 comprising an appropriate salt concentration and/or non-ionic detergent. The appropriate salt concentration is preferably less than 1M sodium chloride (or other salt providing similar ionic strength), and preferably less than 0.6M sodium chloride. Examples of non-ionic detergents which can be used include Tween-20® or Triton X-100® at a concentration of 0.1–5.0% v/v.

The sample may be any sample in which it is desired to detect DNA when it is present at a low concentration. The sample may be a solid or a liquid, such as a proteinaceous lyophilized composition or aqueous medium. Samples can include proteins made by recombinant DNA methods, for example, tissue plasminogen activator, insulin, growth hormone, interleukin 2, and interferons; monoclonal antibodies prepared for therapeutic purposes; water for use in procedures requiring absolute purity. The DNA may be in the form of naked DNA, either double-stranded or single-stranded, or it may be in the form of a whole cell, either prokaryotic or eukaryotic.

The method for carrying out the subject invention generally is as follows, although other variations are within the scope of the invention. If the DNA is contained in whole cells such as bacteria or yeast cells, the cells can be lysed by exposure to lytic conditions such as treatment with sodium hydroxide, chaotropic agents, such as potassium thiocyanate, and the like. If the sample contains protein, the protein is optionally removed. As necessary, the DNA is then denatured to ssDNA.

To detect the DNA in the sample, a number of methods may be used, which include the following. The sample can be combined in an assay medium with BP to form DNA-BP complexes. The BP may be in solution or bound to a solid support. The assay medium is any convenient buffer which will facilitate binding of the various assay components. The ssDNA is then bound non-diffusively to a solid support, for example via binding to BP bound diffusively or non-diffusively to the solid support. The complexes are then freed of any unbound sample and BP, and the complexes detected by means of the label as indicative of the presence of DNA in the sample. If the solid support does not contain non-diffusively bound BP, the ssDNA may be fixed on the solid support by, for example, baking, treatment with ethanol, or other convenient means. BP is then added to the solid support where it binds specifically to the ssDNA. Whether any DNA is present in the sample is determined by detecting ssDNA-BP complexes on the solid support by means of a label, generally bound to either the BP or the ssDNA.

Instead of being bound to the solid support directly the BP may be bound indirectly through a specific binding pair member label bound to the BP which in turn is bound to the solid support via a specific binding pair member, complementary to the specific binding pair member label, which is immobilized on the solid support. Examples of specific binding pairs include biotin and avidin; biotin and streptavidin; and biotin and antibiotin. Following contact of a sample comprising ssDNA with the solid support, a second BP comprising a detectable label is then added and DNA presence determined by means of the detectable label.

When using the assay system where the BP is bound indirectly to the solid support, the components of the assay system may be combined together on a solid support, or added sequentially, including a step after addition of each component to remove any unbound assay components. For example, BP labeled with a specific binding pair member (sbpm) such as biotin is contacted with a solid support comprising a complementary specific binding pair member (s'bpm) such as antibiotin and the solid support washed to remove any unbound specific binding pair members. Sample containing ssDNA is then added where it binds to the BP bound to the solid support. BP comprising a detectable label (dl) such as an enzyme is then added to the solid support where it binds to the ssDNA. Thus the solid support comprises (dl-BP)-ssDNA-(BP-sbpm)-s'bpm complexes. The solid support is then freed of any uncomplexed dl-BP and the presence of DNA determined by means of the detectable label.

When it is desired to determine the concentration of DNA present, in addition to the sample, usually there will be at least one standard solution tested; there will be at least one background solution containing no DNA; and there will be at least one reference solution containing a known amount of DNA; all of which are treated identically to the sample containing an unknown concentration of DNA. The amount of label detectable in the background solution is subtracted from the amount of label detectable in the reference solution and the unknown sample. The adjusted values for the reference solution and the unknown sample are then related to determine the amount of DNA present in the sample.

The following are general methods for carrying out the above steps. The method of the present invention can be used for the detection of DNA in either the presence or absence of protein. When protein is present, an additional step to deproteinize the sample is desirable. Any conventional means for deproteinization can be used (for example, phenol extraction) which does not adversely affect the integrity of the DNA. If the protein has known characteristics, the sample may be deproteinized by ion-exchange column chromatography (for example, DEAE-cellulose, phosphocellulose, sulfonic gel), hydroxyapatite (the single-stranded and double-stranded DNA may be separated from protein by elution with differential salt concentrations), gel filtration, and affinity chromatography.

Affinity chromatography may be used to remove the protein directly from the sample, e.g., using immobilized mouse immunoglobulin raised against the protein to be removed, or the sample may be deproteinized using immobilized BP to bind the DNA in the sample. The DNA can then be eluted from the BP using a high-salt concentration, usually greater than 1M, preferably greater than 2M, and the eluant used directly in the detection assay after adjusting the salt concentration. The final salt concentration varies depending upon the protocol used. For example, where the solid support is a positively charged nylon membrane or a membrane comprising a linker molecule, the salt concentration is adjusted to isotonic. For detection of DNA in a monoclonal antibody sample, the monoclonal antibody may be removed using protein A bound to a solid support.

Other methods of deproteinizing the sample include mixing the sample with a suspension of glass particles in the presence of a high concentration of sodium iodide. Any DNA present in the sample is non-diffusively bound by the glass particles. The glass particles are isolated, and the DNA recovered from the particles by treatment with water or PBS. The glass particles may include finely ground glass beads, or preferably a composition comprising Glassmilk TM as supplied by BIO 101, Inc., La Jolla, Calif.

Another method which can be used to deproteinize the sample is admixing the protein-containing sample with a proteolytic enzyme composition comprising, for example, at least one of the enzymes pronase or proteinase K. Following the enzymatic treatment, hydrolyzed product is optionally removed, for example, by gel filtration or by centrifugation through a membrane with a low molecular weight cutoff (approximately 10,000 or 30,000 as supplied by Centricon-10, Centricon-30; Amicon, Danvers, Mass.); use of a Millipore low-volume ultrafiltration device with a low molecular weight cutoff (approximately 10,000 or 30,000). After any protein present is digested, removed, or digested plus removed, the DNA is denatured to ssDNA. Methods used to denature the DNA include heating at about 90°–100° C. or treatment with sodium hydroxide (pH 13.0). After rapid chilling (to prevent the DNA from reannealing) or neutralization (using for example, ammonium acetate or Tris buffer), the ssDNA is contacted with a solid support.

If the solid support is a membrane such as nitrocellulose or positively-charged nylon, the sample is generally filtered using a manifold filtration device. However, if the solid support is, for example, positively-charged nylon beads, the beads can be incubated directly in the sample. When the solid support has BP immobilized on its surface, the ssDNA binds to the BP to form BP-ssDNA complexes. If the solid support does not contain BP, the DNA is fixed on the solid support by baking, or treatment with ethanol. This step can be omitted when a positively-charged nylon membrane is used.

Non-specific binding sites on nitrocellulose or positively-charged nylon can be blocked by incubation of the membrane or beads with a high-concentration protein solution such as about 1 to 10% bovine serum albumin (BSA), non-fat dry milk solution and the like. For the positively-charged nylon, the non-specific binding sites additionally can be blocked by washing with a non-ionic detergent solution, such as Tween-20 ® or Triton X-100 ®, usually 0.1–5.0%.

The solid support comprising non-diffusively bound ssDNA is then incubated with labeled BP to form BP-ssDNA complexes. When the solid support is a nitrocellulose or positively-charged nylon membrane, buffer (pH 6-9) containing BP (generally about 0.3 µg/ml) is added to the membrane. The buffer is generally at room temperature and contains sodium chloride, preferably 0.01–0.3M, and in addition, for the positively-charged nylon, contains a non-ionic detergent such as Tween-20 ® or Triton X-100 ®, preferably 0.1-5.0% v/v.

Any BP-ssDNA complexes can be detected by means of a label attached to either the BP or the ssDNA, the label preferably being attached to the BP. An exception is when the BP is pre-attached to the solid support, when the DNA is preferably labeled. The BP can be covalently labeled in a number of ways. The label can be an enzyme, for example, alkaline phosphatase, β-D- galactosidase, glucose-6-phosphate dehydrogenase, glucose oxidase, horseradish peroxidase, β-lactamase, urease; a radionuclide, such as $^{125}$I; a chemiluminescent or fluorescent compound, such as fluorescein isocyanate; a hapten such as biotin, and the like; or any other label which provides a detectable signal. When the label is an enzyme such as urease, which contains at least one free, accessible, non-essential cysteine residue. BP can be coupled to the enzyme, for example, as described by Blakely et al., *J. Mol. Catalysis* (1984) 23:263-292). Other enzymes which can be coupled in this way include β-D-galactosidase.

Alternatively, an enzyme label can be thiolated and then conjugated to the BP. Methods for attaching labels to proteins are described in detail in the scientific literature. See for example Healey et al., *Clinica Chimica Acta* (1983) 134:51-58; Ishikawa et al., *J. Immunoassay* (1983) 4:209-327; and Tijssen, *Practice and Theory of Enzyme Immunoassays* (1985) 259-263, Elsevier Science Publishers [Amsterdam].

When the label on BP is an enzyme, it is convenient to use a mercaptan coupling member covralently bounded to the BP for linking mercaptan groups on the enzyme to the BP. In the case of SSB the number of maleimide molecules for mercaptan linking bound per SSB molecule is usually about 1 to 3 maleimide molecules/SSB, preferably 1.8 maleimide molecule/SSB. Generally this results in an SSB-enzyme conjugate comprising 1 enzyme molecule per SSB molecule. When the label is a haptan such as biotin, the number of hapten molecules bound per SSB molecule is usually 1 to 5, preferably 3 to 4.

The DNA to be detected can be labeled, rather than the BP. The label may include a radionuclide, fluorophore, or a hapten such as digoxin or biotin and the like. The label can be introduced to the DNA by any standard enzymatic reaction such as nick translation, or by terminal labeling, with $^3$H, $^{14}$C $^{32}$P, or biotin-labeled deoxynucleotide triphosphates (dNTP). The labeled DNA is then denatured to ssDNA by alkali or heat.

Alternatively, the DNA can be labeled with a reagent such as isopsoralen which binds to double-stranded DNA. $^3$H-isopsoralen or biotin-isopsoralen is available from HRI Research, Inc., Berkeley, Calif. The isopsoralen reagent is bound to DNA by mixing it with a sample, followed by photoirradiation at 340-380 nm. When the label used is isopsoralen, it is unnecessary to denature further the labeled DNA, as isopsoralen-labeled DNA is recognized by BP without any additional denaturing step.

Methods of detecting BP-ssDNA complexes will depend on the type of label used as well as the sensitivity required. When the label is an enzyme, the disappearance of substrate or appearance of reaction product may be measured spectrophotometrically following substrate addition. If the enzyme is, for example, urease, an indicator dye such as cresol red may be used to monitor the change in pH in the sample following addition of enzyme substrate. The change in optical density or the visual intensity of the color change is then correlated with the DNA content of the sample by comparison with at least one identically treated reference solution containing a known concentration of DNA. Alternatively, any DNA present may be detected by measuring the amount of pH or potential change with a photoresponsive device such as that described in U.S. Pat. No. 4,591,550. Other methods of detecting BP-ssDNA complexes in the sample may include quantitating the amount of radioactivity, when the label is a radionuclide. When the label is a hapten such as biotin, the label can be detected by, for example, the use of enzyme-labeled avidin, streptavidin or antibiotin.

Various protocols may be used. For example, a sample suspected of containing an organism or free DNA may be lysed in the former case, and in both cases denatured to provide ssDNA. The sample may then be contacted with a positively charged nylon membrane or a membrane to which a high affinity ssDNA binding protein is conjugated. Any DNA may then be detected by employing an ssDNA binding protein conjugate bonded to a detectable label.

For convenience, the reagents are frequently provided in kits, where they may be present in conjunction with buffer, stabilizers, excipients and the like. The kit may also include any additional reagents necessary for the preparation of labeled BP or ssDNA and the detection of the labeled BP-ssDNA complexes in the performance of the assay. Where the reagents include BP, it may be provided labeled or unlabeled. When unlabeled, it may also be provided bound non-diffusively to a solid support.

The following examples are offered by way of illustration and not by way of limitation.

EXPERIMENTAL

Example 1

Preparation of SSB-Enzyme Conjugates

A. Preparation of SSB Urease Conjugate Using m-Maleimidobenzoyl N-hydroxysuccinimide Ester (MBS)

Single-stranded DNA binding protein from *E. coli* (SSB) was obtained from United States Biochemical Corp. Cleveland, Ohio. It was coupled to the cross-linking agent MBS as follows. One hundred μl of 0.25% MBS in dimethylformamide (DMF) was added to 2.0 ml containing 2 mg of SSB in 0.1M phosphate buffer, pH 6.8. The mixture was stirred gently at room temperature for 30 min then separated on a Sephadex G-25. The elution buffer was 0.1M phosphate, pH 6.8. Fractions were monitored by UV absorbance at 280 nm. The first peak eluted from the column contained SSB coupled to MBS. The peak fractions (3 ml) were combined with 4 ml of urease (20 mg) in 0.1 M phosphate buffer, pH 6.8. The mixture was stirred for 20 min at room temperature. The reaction was then stopped by the addition of 1.75 ml of 500 mM sodium sulfite, in 0.1M sodium phosphate buffer, pH 6.8, containing 10 mM dithiothreitol (DTT). The conjugate formed was either used directly in the assay or was separated from unconjugated enzyme by gel filtration chromatography. The purified enzyme conjugate was then diluted 1:1 (v/v) with glycerol. BSA was added to 0.25% (w/v). The conjugate was stored at 2°-8° C.

B. Preparation of SSB Horseradish Peroxidase (HRP) Conjugate Using m-maleimidobenzoyl N-hydroxy-succinimide ester (MBS)

HRP (Boehringer-Mannheim, La Jolla, Calif.) was thiolated with N-succinimidyl 3-(2-pyridyldithio)propionate (SPDP) (Pierce, Rockville, Ill.) by combining 16 mg HRP in 0.1M potassium phosphate buffer, 0.2M sodium chloride, pH 7.5 with 435 μg SPDP in 25 μl dimethylformamide (DMF), and incubating for 30 min at room temperature. Unreacted SPDP was removed by chromatography on Sephadex G-25, and eluted with 0.1M potassium phosphate buffer containing 0.2M sodium chloride, pH 7.0.

Dithiopyridine groups on HRP were deblocked by adding 25 mM DTT for 30 min, then removing the DTT and the 2-thiopyridine formed by G-25 separation in PBS.

Maleimido-SSB was formed by adding 25 μl of a 0.25% solution of MBS in DMF to 0.55 mg of SSB in 0.5 ml of 0.1M sodium phosphate buffer, and stirring for 30 min at room temperature. Maleimido-SSB was purified on Sephadex G-25, then condensed with 15 mg of thiolated HRP by combining the two solutions and reacting for 20 min at room temperature. The reaction was stopped by addition of 12.5 μl of 100 mM 2-mercaptoethanol. The SSB-HRP conjugate solution was made 10% (v/v) in glycerol and stored at 4° C.

C. Preparation of SSB-Biotin Conjugate.

One mg of SSB in PBSE (150 mM sodium phosphate pH 7.0, NaCl 50 mM, and 1 mM EDTA) was mixed with 50 μg of biotinamidocaproate N-hydroxysuccinimide ester in 20 μl of DMF for 2 hrs at room temperature with stirring. Unreacted biotin reagent was removed by passage over a Sephadex G-25 column.

D. Preparation of Anti-DNA-Urease Conjugate

One mg of purified anti-DNA monoclonal antibody, clone 4H2 (obtained from Dr. Richard Weisbart at the Sepulveda Veterans Administration Hospital, Los Angeles) in 1 ml PBSE was reacted with 125 μg of 4-(N-maleimido methyl) cyclohexane-1-carboxylic acid N-hydroxysuccinimide ester (SMCC) in 50 μl of DMF. Unreacted SMCC was removed by passage over a Sephadex G-25 column eluted with PBSE. The number of maleimide groups per antibody was 4. Urease (20 mg) was then added to the maleimide-antibody and incubated for 4 hr at 4° C. Unreacted maleimide groups were then blocked by addition of 2-mercaptoethanol to a concentration of 2 mM.

Conjugate was purified by gel filtration chromatography on a 1.5 cm × 70 cm column of Sephacryl S-400 HR (Pharmacia, Piscataway, N.J.) in a buffer composed of 50 mM sodium sulfite, 20 mM sodium dihydrogen phosphate, 200 mM sodium chloride, 1 mM EDTA, 2 mM dithiothreitol and 0.1% Tween-20. The entire protein peak eluting ahead of the free urease peak was combined. 0.05% BSA was added and the conjugate solution was stored at 4° C. in sealed containers under argon gas.

E. Preparation of Biotin-Anti-DNA Conjugate

One mg of purified anti-DNA monoclonal antibody obtained from R. Weisbart in PBSE was added to 50 μg of biotin amido caproate-N-hydroxysuccinimide ester in 20 μl DMF and stirred for 2 hrs at room temperature. Unreacted biotin reagent was removed by passage over a Sephadex G-25 column. Purified anti-DNA-biotin was stored at 4° C.

Example 2

Binding of SSB to Solid Supports

A. Immobilization of SSB on an Immobilon TM Membrane

Immobilon TM membrane contains carbonyl imidazole groups which bind to epsilon amino groups on lysine or arginine. SSB was immobilized on a 0.65μ Immobilon TM membrane (Millipore; Bedford, Mass.) by soaking the membrane in phosphate buffered saline containing 0.2 mg/ml SSB at room temperature for 1 hour (10 cc protein solution/ 100 cm² membrane). The SSB solution was removed by decanting. Any remaining active carbonyl imidazole groups on the membrane were quenched with 0.1M ethanolamine (pH 9.5) at room temperature overnight. The membrane was then washed successively in phosphate buffered saline, distilled water, and polyvinylalcohol (15 min each wash), and then dried at 65° C. for 5 min. The dried membrane was then ready for use in the detection system. Four hundred μl of a sample containing single-stranded $^{32}$P-labeled DNA (from 10–1000 pg) in a 10 mg/ml BSA aqueous solution was filtered through the SSB-Immobilon TM membrane (filtration time of 10 min). Seventy percent of the $^{32}$P counts were captured on the membrane when the SSB concentration was 0.2 mg/ml. Increasing the SSB concentration used in the immobilization procedure to 1 mg/ml improved the DNA capture to 80%.

B. Immobilization of SSB on Nitrocellulose Membranes

SSB was adsorbed to a nitrocellulose membrane (0.45μ pore size, Schleicher and Schuell) by soaking the membrane in PBS containing 50 μg/ml SSB at 4° C. overnight. Non-specific binding sites on the membrane were blocked with 10 mg/ml BSA at room temperature for 1 hour. When 400 μl of samples containing 10 mg/ml BSA and $^{32}$P-labeled single-stranded DNA were filtered through the membrane, 36% of the $^{32}$P counts were captured on the nitrocellulose membrane.

Example 3

Detection of Pure DNA in a Sample

A. Visual Determination

Samples containing pure calf thymus DNA (Sigma Chemical Co., St. Louis, Mo.) from 0–100 pg/sample (in 10 mM sodium phosphate, pH 7.0, 0.15M sodium chloride, mM EDTA) were denatured to single-stranded DNA by heating at 100° C. for 10 min followed by rapid chilling. The denatured samples were filtered through 0.45μ nitrocellulose membrane (Schleicher and Schuell; Keene, N.H.) using a manifold filtration device. The membranes were then baked at 80° C. for 1 hour to fix the DNA. SSB-urease conjugate, prepared as in Example 1A and used without further purification, was diluted to 0.3 μg/ml in 2% bovine serum albumin (BSA), 2% Ficoll, 2% polyvinylpyrrolidone, 10 mM sodium phosphate, 40 mM sodium chloride, 2 mM EDTA, pH 7.5 was added to the membrane. The membrane was incubated with the SSB-urease conjugate for 1 hour at room temperature in a Petri dish in a sufficient volume of conjugate to cover the membrane. The membrane was then washed three times with 0.15M sodium chloride, 1 mM EDTA (pH 6) to remove any non-specifically bound conjugate. Any DNA present was then detected by the addition of enzyme substrate (100 mM urea, 0.15M sodium chloride, 1 mM sodium phosphate, pH 6, 0.5 mM cresol red). The change in pH due to the urease reaction resulted in a color change of the cresol red from orange to purple-red. The visual intensity of the purple-red spot was then correlated with the DNA content of the sample by determining the relative size of the colored spots on the membrane and the intensity of the color.

TABLE 1

| COLORIMETRIC DETECTION OF DNA | |
|---|---|
| Pure DNA (pg/sample) | Intensity of Color at 3 min |
| 0 | — |
| 10 | + |
| 20 | ++ |
| 50 | +++ |

TABLE 1-continued

COLORIMETRIC DETECTION OF DNA

| Pure DNA (pg/sample) | Intensity of Color at 3 min |
|---|---|
| 100 | ++++ |

B. Biosensor pH determination

Any DNA present on membranes prepared as described above can also be detected by measuring the amount of pH change following addition of enzyme substrate, using a photoresponsive device (see for example U.S. Pat. No. 4,591,550). An enzyme substrate mixture containing 1 mM sodium phosphate, 0.05% Tween-20, 100 mM urea, pH 6 was added to the membranes. The change in pH due to the urease reaction resulted in a change in the signal of the photoresponsive device. The change in the signal (in $\mu$volt/ sec) was then correlated with the DNA content of the sample.

TABLE 2

DETECTION OF DNA BY BIOSENSOR pH DETERMINATION

| DNA (pg/sample) | $\mu$volt/sec |
|---|---|
| 0 | 64 |
| 12 | 107 |
| 25 | 153 |
| 50 | 268 |
| 100 | 341 |

Example 4

Preparation of Solid Supports for Specific Capture of DNA

A. Preparation of Anti-Biotin Membrane

1. Nitrocellulose

Anti-biotin (Sigma) was dissolved in PBS at a concentration of 0.25 mg/ml. A nitrocellulose sheet (0.8$\mu$) (Schleicher and Schuell) was wetted with DNA-free water, then incubated in the anti-biotin mixture (0.2 ml/cm$^2$ membrane) with gentle rocking membrane for 15 min at room temperature, then overnight at 4° C. The anti-biotin mixture was then poured off and the nitrocellulose rinsed briefly with PBS (0.2 ml/cm$^2$). The nitrocellulose was then incubated with 0.1% (w/v) glutaraldehyde in PBS for 15 min. The nitrocellulose was then washed successively with PBS, then DNA-free water, both at 0.2 ml/cm$^2$. The nitrocellulose was then wetted with 0.2% (w/w) polyvinyl alcohol for 10 min at 0.2 ml/cm$^2$. The nitrocellulose was then baked for 10 min at 60° C.

2. Cellulose acetate

An anti-biotin membrane was prepared as described in Section 3A.1, above, substituting a cellulose acetate membrane (Schleicher and Schuell, 1.2$\mu$pore size), except that the wash with PBS prior to the glutaraldehyde/PBS incubation was omitted.

Example 5

Detection of DNA in Samples Containing Protein with Nitrocellulose Membrane

A. Protein removal by glass beads

Four hundred $\mu$l of sodium iodide (6M) were added to 200 $\mu$l of samples, each containing 2 mg of BSA and 100, 50, 25, or 0 pg calf thymus DNA. Two $\mu$l of Glassmilk TM were added and the mixture incubated for 10 min at room temperature. The Glassmilk TM /DNA complex was pelleted by centrifugation for 10 sec in a microcentrifuge. The pellet was washed with 150 $\mu$l 20 mM Tris buffer, containing 200 mM sodium chloride, 2 mM EDTA in 55% methanol. The wash procedure was repeated once. After the DNA was eluted with 400 $\mu$l phosphate buffered saline, each sample was heated at 100° C. for 10 min to denature the DNA then rapidly chilled. The sample was filtered onto nitrocellulose membranes. DNA was detected using the visual determination procedure described in Example 3.A.

TABLE 4

DETECTION OF PROTEIN-CONTAINING SAMPLES

| DNA DNA (pg/sample) | Intensity of Color at 3 min |
|---|---|
| 0 | slight positive |
| 25 | ++ |
| 50 | +++ |
| 100 | ++++ |

B. Protease digestion of protein

Proteinase K and dithiothreitol were added (final concentration 100 $\mu$g/ml and 50 mM, respectively) to 100 $\mu$l of samples each containing 1 mg BSA and 100, 50, 25, 12, or 0 pg of DNA in phosphate buffered saline. The mixture was incubated at 55° C. for 2 hours to digest the protein. After digestion, all samples were heated at 100° C. for 5 min to inactivate proteinase K and denature DNA to single-stranded DNA. Control samples containing a matching amount of DNA but no protein were denatured at the same time. Each sample, after rapid chilling to prevent reannealing of the DNA, was filtered through a nitrocellulose membrane. Visual determination procedures were carried out as described in Example 3.A to detect the presence of DNA.

TABLE 5

DETECTION OF PROTEINASE-DIGESTED, PROTEIN-CONTAINING SAMPLES

| DNA (pg/sample) | Intensity | |
|---|---|---|
| | With Protein | Without Protein |
| 0 | − | − |
| 12 | + | + |
| 25 | ++ | ++ |
| 50 | +++ | +++ |
| 100 | ++++ | ++++ |

Example 6

Detection of DNA in Sample Containing Protein by Adsorption of the DNA to Positively Charged Nylon 7.5 $\mu$l of proteinase K (2 mg/ml) were then added to 150 $\mu$l solution of porcine insulin (Cal Biochem, La Jolla, Calif.) 10 mg/ml in 10 mM TRIS-HCl 1 mM EDTA, pH 8.7, containing 0, 5, 10, 20, or 40 pg of double-stranded calf thymus DNA. The samples were incubated overnight at 55° C., boiled at 100° C. for 5 min, then chilled on ice. The digested samples were then filtered through a positively charged nylon membrane (Genatran TM , 6 cm×8 cm obtained from Plasco, Inc., Woburn, Mass.) at a rate of about 100 $\mu$l/min. DNA was detected by incubating the membrane with 0.2-0.5 ml/cm$^2$ SSB-HRP conjugate (150 ng/ml in 50 mM sodium phosphate, pH 7.4; 150 mM NaCl; 2 mM EDTA, 0.1 mg/ml BSA; 5% Triton-X 100 ®) for 40 min at room temperature in a petri dish. The membrane was then washed three times by incubating the membrane in PBS containing 1M urea and 1% dextran sulfate for 3 min each wash to remove any non-specifically bound SSB-HRP. The membrane was then washed with distilled water, incubated for 10 min in 10 mM sodium citrate buffer containing 10 mM EDTA, 0.1 mg/ml tetramethyl benzidine and 0.001% hydrogen peroxide, pH 5. The visual intensity of the blue spots which developed on the membrane was determined subjectively, then correlated with the DNA content of the original sample. The results were as shown in Table 6.

TABLE 6

VISUAL DETECTION OF DNA USING SSB-HRP

| pg of DNA in Insulin Sample | Intensity of Color |
|---|---|
| 40 | ++++ |
| 20 | ++ |
| 10 | + |
| 5 | slight positive |
| 0 | — |

Example 7

Detection of DNA Using Specific Capture of Sample DNA on an Anti-Biotin Membrane A. Purification of SSB-Urease Conjugate In this example, SSB-urease was further purified to remove unconjugated urease by gel filtration chromatography of the SSB-urease on a column of 1 cm×30 cm of Superose 6 (Pharmacia, Piscataway, N.J.) in a buffer containing 50 mM sodium sulfite, 20 mM sodium dihydrogen phosphate, 200 mM sodium chloride, 1 mM EDTA, 2 mM dithiothreitol, 0.1% Tween-20 pH 7.00. The protein peak eluting before the unconjugated urease peak was collected and combined with glycrol 1:1 (v:v) and stored at −20° C.

B. Biosensor Detection of DNA in Buffer with SSB-Urease Conjugate (Sequential Addition of Reagents)

Anti-biotin-coated nitrocellulose membranes prepared as described in Example 4A1, were coated with biotin-anti-DNA by filtering 200 μl of biotin-anti-DNA (see Example 1E), in 300 ng/ml in 10 mM TRIS-HCl containing 1% BSA, 1 mM EDTA through the antibiotin membrane over a period of about 4 min. The membranes were then washed with 300 μl PBS. 200 μl of the samples containing DNA (0, 12, 25, 50 pg/200 μl DNA in PBS) were filtered over a period of about 4 min. The filter was again washed with 300 μl of PBS. Over about 4 min, 200 μl of SSB-urease conjugate, purified as described in Example 7A, (100 ng/ml diluted in 2% BSA, 2% Ficoll ®, 2% polyvinylpyrrolidone, 10 mM sodium phosphate, 40 mM NaCl 2 mM EDTA, pH 7.5) was filtered through the membrane. The membrane was then washed 3 times with 1 ml of 1 mM sodium acetate, 0.1M NaCl, 0.05% Tween-20, pH 5. The membrane was added to substrate solution (acetate wash buffer containing 100 mM urea) and the rate of product formation measured as described above in Example 3B. The rate of product formation was a function of the concentration of DNA in the sample, as shown in Table 7.

TABLE 7

BIOSENSOR DETECTION OF DNA USING SSB UREASE CONJUGATE

| Amount of DNA (pg) | Rate (uV/sec) |
|---|---|
| 50 | 546 |
| 25 | 300 |
| 12 | 183 |

TABLE 7-continued

BIOSENSOR DETECTION OF DNA USING SSB UREASE CONJUGATE

| Amount of DNA (pg) | Rate (uV/sec) |
|---|---|
| 0 | 120 |

C. Titration of Biotin-Anti-DNA for a Simultaneous-Incubation Assay

The effect of simultaneously adding biotin-anti-DNA and SSB-urease conjugate purified as described in Example 7A to the antibiotin coated nitrocellulose membrane was assessed as follows:

200 μl of sample (1% BSA in TE with or without 100 pg ssDNA) was incubated with 200 μl biotin-anti-DNA (40, 81, 162, 325 ng/ml in 1% BSA, TE) and 200 μl SSB-urease conjugate (15 ng/ml in 2% BSA, 2% Ficoll ®, 2% polyvinylpyrrolidone, 10 mM sodium phosphate, 40 mM NaCl, 2 mM EDTA, pH 7.5) at room temperature for 50 min. The mixture was then filtered slowly over a period of about 10 min through an antibiotin coated nitrocellulose membrane (see Example 4.A.1). The membrane was then washed 3 times with 1 ml of acetate wash buffer (1 mM sodium acetate, 0.1M NaCl, 0.05% Tween-20, pH 5). Substrate solution (acetate wash buffer containing 100 mM urea) was added and the amount of DNA present on the membrane determined using the biosensor procedure as described above in Example 3B. The results, shown in Table 8 below, show that in a simultaneous assay, the ratio of biotin-anti-DNA and SSB-urease conjugate is critical, presumably due to competition of both anti-DNA and SSB for DNA.

TABLE 8

TITRATION OF BIOTIN-ANTI-DNA THROUGH SIMULTANEOUS-INCUBATION ASSAY

| Concentration of Biotin-Anti-DNA (ng/ml) | Rate (uV/sec) | |
|---|---|---|
| | 100 pg DNA | No DNA |
| 325 | 308 | 108 |
| 162 | 476 | 149 |
| 81 | 1046 | 238 |
| 40 | 1308 | 217 |

D. Biosensor Detection of DNA in Granulocyte Macrophage Colony Stimulating Factor (GM-CSF) Samples with SSB-HRP Conjugate (Sequential Addition)

300 μl of recombinant human GMCSF (Biogen, Cambridge, Mass.), 3.4 mg/ml PBS, was spiked with 0, 5, 10, 50, or 100 pg double-stranded calf thymus DNA. The samples were heated to 100° C. for 5 min to denature the DNA, then cooled to room temperature. Immobilon ™ membranes (Millipore, Bedford, Mass.) were coated with goat anti-biotin IgG (Sigma, St Louis, Mo.), as described above for SSB coating on Immobilon ™ in Example 2A. 200 μl of biotin-labeled anti-DNA (clone 4H2) was filtered through the membrane. 300 μl of the samples containing GMCSF were filtered through the membranes and the membranes washed again with 200 μl of PBS. 200μl of SSB-HRP conjugate (650 ng/ml, diluted in PBS containing 0.1 mg/ml BSA, 2 mM EDTA, 5% Triton-X 100) was filtered through the membrane. Membranes were then washed once with PBS containing 5% Triton-X 100, 1M urea, and washed with 0.1M sodium acetate, containing 5% ethanol and 1 mM EDTA, pH 5.5. The amount of DNA was then determined by the biosensor method as described above in U.S. Pat. No. 4,591,550, which disclosure is incorporated herein by reference. The substrate solution comprised sodium acetate wash buffer containing 250 $\mu$M tetramethyl benzidine, 50 $\mu$M ruthenium, 500 $\mu$M hydrogen peroxide, pH 5.5. The change in potential due to the HRP redox reaction resulted in a change in the signal of the photoresponsive device. The results were as shown in Table 9, below.

TABLE 9

BIOSENSOR DETECTION OF DNA IN GM-CSF SAMPLES USING SSB-HRP CONJUGATE

| pg of DNA in 1 mg GMCSF (3 mg/ml) | Rate ($\mu$V/sec) |
|---|---|
| 0 | −137 |
| 5 | −201 |
| 10 | −268 |
| 50 | −629 |
| 100 | −1550 |

Example 9

Detection of Bacteria in a Water Sample

Cultures of gram-negative and gram-positive bacteria are diluted in 100 $\mu$l HPLC-grade water to 80, 400, 2,000, 10,000/100 $\mu$l. For one set of samples, the bacteria are lysed and denatured by treatment with 10 $\mu$l of 3N NaOH, then neutralized with 50 $\mu$l of 1M TRIS-HCl, pH 7.3. A second identical set of dilutions was not so treated and serve as a control for non-specific interaction between the sample and the SSB-HRP conjugate.

Both sets of dilutions are loaded onto a positively charged nylon membrane (Genatran ™) using a dot-blot apparatus (Schleicher and Schuell). Each well of the apparatus is loaded with 165 $\mu$l of sample. Standards, consisting of denatured calf thymus DNA diluted in HPLC-grade water) are also prepared and loaded onto the positively charged nylon membranes. Standards contain 0, 5, 10, or 50 pg ssDNA. DNA is detected using the visual assay as described above in Example 3A using an SSB-HRP conjugate.

The subject methods and compositions provide a rapid and simple means for detecting picogram amounts of DNA in a sample by the use of high affinity single-stranded DNA binding proteins. The assay is applicable not only to pure DNA samples but may also be used with samples which contain a significant amount of protein, or for detecting contamination of a sample with a microorganism.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A conjugate comprising a high affinity single-stranded DNA binding protein (BP) covalently linked to a detectable label (dl), wherein said conjugate is capable of binding with high affinity via said BP directly to DNA to be detected.

2. The conjugate according to claim 1, wherein said BP is single-stranded DNA binding protein, T4 gene 32 protein, or topoisomerase I.

3. The conjugate according to claim 2, wherein said enzyme is urease or horseradish peroxidase.

4. The conjugate according to claim 1, wherein said dl is an enzyme.

5. A conjugate comprising a high affinity single-stranded DNA binding protein (BP) covalently linked to a specific binding pair member (sbpm), wherein said conjugate is capable of binding with high affinity via said BP directly to DNA to be detected.

6. The conjugate according to claim 5, wherein said sbpm is biotin, avidin, streptavidin or antibiotin.

* * * * *

UNITED STATES PATENT AND TRADEMARK OFFICE
CERTIFICATE OF CORRECTION

PATENT NO. : 4,963,658

DATED : October 16, 1990

INVENTOR(S) : Viola T. Kung and Peter A. Nagainis

It is certified that error appears in the above-identified patent and that said Letters Patent is hereby corrected as shown below:

At column 9, line 16, change "150" to "50".

At column 9, line 17, change "NaCl 50 mM" to "150 mM NaCl".

Signed and Sealed this

Thirtieth Day of June, 1992

Attest:

DOUGLAS B. COMER

Attesting Officer

Acting Commissioner of Patents and Trademarks